United States Patent [19]

Shimizu et al.

[11] Patent Number: 4,694,100

[45] Date of Patent: Sep. 15, 1987

[54] METHOD FOR PRODUCING α-(P-ISOBUTYLPHENYL)PROPIONIC ACID OR ITS ALKYL ESTERS

[75] Inventors: Isoo Shimizu; Ryotaro Hirano; Yasuo Matsumura; Hideki Nomura; Kazumichi Uchida, all of Yokohama; Atsushi Sato, Tokyo, all of Japan

[73] Assignee: Nippon Petrochemicals Company, Ltd., Tokyo, Japan

[21] Appl. No.: 753,403

[22] Filed: Jul. 10, 1985

[30] Foreign Application Priority Data

Jul. 14, 1984 [JP] Japan .................................. 59-146594
Jul. 14, 1984 [JP] Japan .................................. 59-146595

[51] Int. Cl.$^4$ ...................... C07C 51/29; C07C 51/14; C07C 67/38
[52] U.S. Cl. .................................. 560/105; 562/406; 562/419; 568/429
[58] Field of Search ................. 562/406, 419; 560/105; 585/439; 568/429

[56] References Cited

U.S. PATENT DOCUMENTS

| | | | |
|---|---|---|---|
| 2,420,689 | 5/1947 | Sturrock | 585/439 |
| 2,422,318 | 6/1947 | Sturrock | 585/439 |
| 2,864,872 | 12/1958 | Saunder | 585/439 |
| 2,954,413 | 9/1960 | Kroeper | 585/439 |
| 4,257,973 | 3/1981 | Mrowca | 562/406 |
| 4,329,507 | 5/1982 | Takeda | 562/406 |
| 4,439,618 | 3/1984 | Cometti | 562/406 |

FOREIGN PATENT DOCUMENTS

| | | | |
|---|---|---|---|
| 2646792 | 4/1977 | Fed. Rep. of Germany | 560/105 |
| 52-62233 | 5/1977 | Japan | 568/429 |
| 53-18534 | 2/1978 | Japan | 562/419 |

OTHER PUBLICATIONS

Olah, "Friedel–Crafts and Related Reactions," vol. II, Part 1, pp. 610–613 & 625–640, (1964).
Falbe, "Carbon Monoxide in Organic Synthesis," pp. 3–40, 78–87 & 99–112, (1967).

*Primary Examiner*—Michael L. Shippen
*Attorney, Agent, or Firm*—Scully, Scott, Murphy & Presser

[57] ABSTRACT

A method for producing α-(p-isobutylphenyl)propionic acid or its alkyl esters which is characterized in that starting materials are inexpensive, processes are easy to be done and products are highly pure. The method comprises the steps of (I): catalytically cracking 1,1-bis(p-isobutylphenyl)ethane at temperatures in the range of 200° to 650° C. in the presence of a protonic acid catalyst and/or a solid acid catalyst to produce isobutylbenzene and p-isobutylstyrene; and (II): reacting said p-isobutylstyrene with carbon monoxide and water or alcohol at temperatures in the range of 40° to 150° C. in the presence of a metal complex carbonylation catalyst to produce α-(p-isobutylphenyl)propionic acid or its alkyl ester; or (III): reacting said p-isobutylstyrene with carbon monoxide and hydrogen at temperatures in the range of 40° to 150° C. in the presence of a metal complex carbonylation catalyst to produce α-(p-isobutylphenyl)propionaldehyde and then oxidizing said α-(p-isobutylphenyl)propionaldehyde to produce α-(p-isobutylphenyl)propionic acid. The recovered isobutylene is recycled to produce 1,1-bis(p-isobutylphenyl)ethane by reaction with acetaldehyde in the presence of sulfuric acid.

33 Claims, 1 Drawing Figure

METHOD FOR PRODUCING α-(P-ISOBUTYLPHENYL)PROPIONIC ACID OR ITS ALKYL ESTERS

BACKGROUND OF THE INVENTION (1) Field of the Invention

This invention relates to a method for producing α-(p-isobutylphenyl)propionic acid or its alkyl esters. More particularly, the invention relates to a novel method for economically producing the above compounds in a pure form.

As disclosed in British Pat. No. 971,700 and French Pat. No. 1,549,758, α-(p-isobutylphenyl)propionic acid (hereinafter referred to as "IPA") is known as a useful medicine for the relief of pain, fever and inflammation.

(2) Description of the Prior Art

IPA and its alkyl esters (hereinafter referred to as "IPE" have been synthesized from various kinds of starting materials by several methods.

In order to prepare IPA and IPE in a pure form at low cost, the following conditions are required (a) To use simple compounds as starting materials;

(b) To employ a series of reactions in which intermediate compounds are also simple and stable;

(c) To employ reactions that do not cause isomerization because the isobutyl group is liable to be isomerized; and (d) To use inexpensive reagents and catalysts.

In the methods for synthesizing IPA or IPE as disclosed in U.S. Pat. Nos. 3,385,886; 3,385,887 and 4,329,507, however, intricate and expensive substances are used as starting materials or unstable and intractable reagents such as Grignard reagents are used so that these methods cannot be regarded as inexpensive and economical.

Furthermore, in the methods disclosed in French Pat. No. 1,549,758 and the above U.S. Patents, p-isobutylacetophenone is used as a starting material.

The p-isobutylacetophenone, however, is not an inexpensive compound as described below. It is most economical to synthesize the p-isobutylacetophenone from isobutylbenzene but the conversion itself of isobutylbenzene into p-isobutylacetophenone is not desirable in an economical view point. That is, an expensive and unstable material of acetyl chloride must be used in the conversion into p-isobutylacetophenone. In addition, a large quantity of, i.e. at least equimolecular amount (to acetyl chloride) of anhydrous aluminum chloride that is quite susceptible to moisture, must be used. For example, assuming that the conversion rate is stoichiometrically 100%, anhydrous aluminum chloride as much as 700 kg is to be used for producing 1,000 kg of p-isobutylacetophenone. In addition, waste materials of 410 kg of aluminum hydroxide and 750 kg of chlorine ions are produced as a result of the deactivation of anhydrous aluminum chloride and the waste materials that exceed the quantity of aimed p-isobutylacetophenone must be treated into innoxious substances. Accordingly, it goes without saying that p-isobutylacetophenone is quite expensive as a starting material. Furthermore, the conversion from p-isobutylacetophenone into α-(p-isobutylphenyl)propionaldehyde must be done via intricate intermediate compounds which is not economical in an industrial viewpoint.

BRIEF SUMMARY OF THE INVENTION

It is, therefore, the primary object of the present invention to provide an improved method for producing α-(p-isobutylphenyl)propionic acid or its alkyl esters which is free from the above described disadvantages in the conventional art.

Another object of the present invention is to provide an improved method for producing α-(p-isobutylphenyl)propionic acid or its alkyl esters from inexpensive starting materials without any difficult procedure.

According to the present invention, the method for producing α-(p-isobutylphenyl)propionic acid (IPA) or its alkyl esters (IPE) is characterized in that the method comprises the following steps (I), (II) and (III). Preparation Step of the Starting Compound:

Isobutylbenzene (hereinafter referred to as "IBB") and acetaldehyde are reacted in the presence of sulfuric acid catalyst to produce 1,1-bis(p-isobutylphenyl)ethane (hereinafter referred to as "BBE").

Step (I):

The above obtained BBE is subjected to catalytic cracking at temperatures of 200° to 650° C. in the presence of a protonic acid and/or a solid acid catalyst to produce IBB and p-isobutylstyrene (hereinafter referred to as "PBS") as main products.

Step (II):

The above obtained PBS, carbon monoxide and water or alcohol are reacted at 40° to 150° C. in the presence of a metal complex carbonylation catalyst to produce IPA or its alkyl ester, IPE.

Step (III):

Or in place of the above step (II), the above obtained PBS, carbon monoxide and hydrogen are reacted at 40° to 150° C. in the presence of a metal complex carbonyl catalyst to produce α-(p-isobutylphenyl)propionaldehyde (hereinafter referred to as "IPN"), and it is then oxidized to produce IPA.

The above processes are represented by the following reaction formulae:

Preparation Step of Starting Compound:

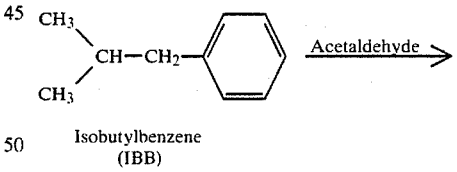

Isobutylbenzene (IBB)

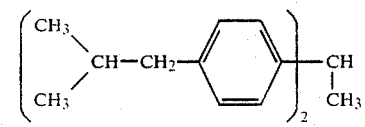

1,1-Bis(p-isobutylphenyl)ethane (BBE)

Step (I):

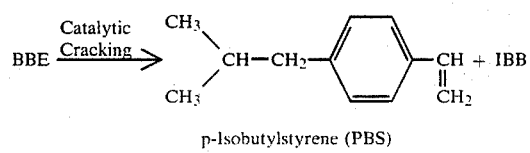

p-Isobutylstyrene (PBS)

Step (II):

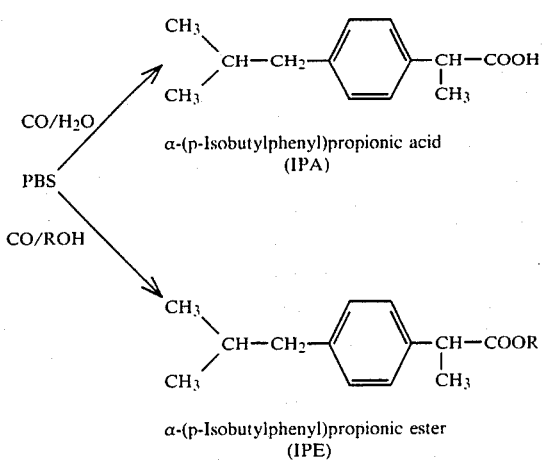

Step (III):

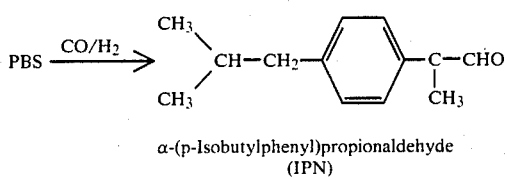

$\xrightarrow{\text{Oxidation}}$ α-(p-Isobutylphenyl)propionic acid (IPA)

According to the present invention, IPA or IPE can be easily produced by only two steps from BBE which is produced from IBB, and acetaldehyde, that are all industrially available in bulk at lower costs.

Furthermore, by adopting the process using the new compound of BBE as a starting compound, IBB (i.e., the starting material of the BBE preparation step) as well as PBS can be obtained as the cracked compounds of BBE. Therefore, the method of the present invention can be made economically advantageous owing to the recycling of the IBB.

DETAILED DESCRIPTION OF THE INVENTION

Figure 1:
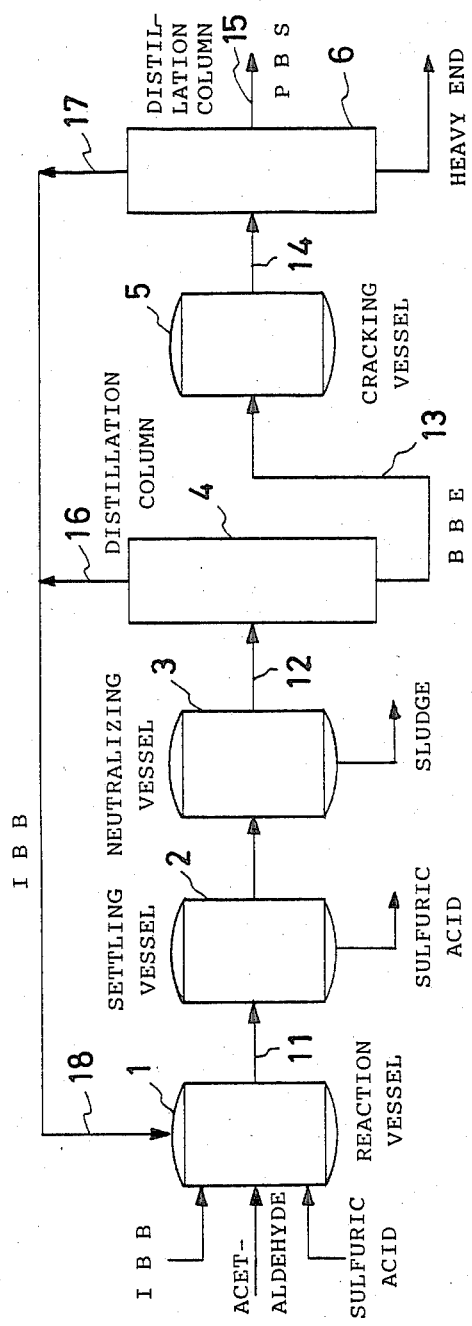
FIG. 1 is a flow sheet showing the starting compound (BBE) preparation step and step (I) in the method of the present invention.

In the following, the method to carry out each step will be described in more detail.

In the method of the invention, the starting material of BBE may be any of those prepared by other methods. The 1,1-bis(p-isobutylphenyl)ethane (BBE) is produced, for example, from IBB. It is inevitable in this step that the yield is high, the isobutyl groups in IBB are not isomerized and BBE is produced with a good selectivity with respect to p-position.

For example, in the known methods in general for producing diarylalkanes from IBB to use acetylene with catalysts of sulfuric acid or both sulfuric acid and mercury; to use 1,1-dichloroethane or vinylchloride with a halogenated metal catalyst; or to use acetaldehyde with a catalyst of phosphoric acid or a complex of phosphoric acid and halogenated metal, the yield of BBE is very low, which is not practical. Furthermore, the methods are not desirable because isomerization of isobutyl groups occurs and reaction products contain much m-position-substituted compounds in addition to the aimed BBE.

All the above disadvantages could be eliminated only when IBB was reacted with acetaldehyde in the presence of sulfuric acid catalyst. As a result, the requirements for the yield and the selectivity to p-position have been satisfied simultaneously and thus it has been made possible to produce BBE.

The concentration of sulfuric acid in the reaction system is maintained at 75% by weight or higher (to sulfuric acid plus water) and it is preferably in the range of 80 to 95% by weight. If the concentration of the sulfuric acid is higher than 95% by weight, not only polymerization products are formed but also side reactions such as sulfonation of aromatic nuclei of IBB is caused to occur, therefore, the object cannot be attained effectively. If the concentration of the sulfuric acid is lower than 75% by weight, the reaction does not proceed well and the concentration of aldehyde in the reaction system becomes high, which undesirably increases the formation of polymers or the intermediate compound, 1-(p-isobutylphenyl)ethanol.

Because this reaction is a dehydration reaction, water is produced with the progress of the reaction and the concentration of sulfuric acid in the reaction mixture becomes low with the progress of the reaction, thus the reaction will be retarded. Accordingly, it is necessary that the concentration of sulfuric acid in sulfuric acid solution in the reaction system should be maintained at the above prescribed level.

For this purpose, it is desirable to add concentrated sulfuric acid continuously during the reaction. Besides the concentrated sulfuric acid, fuming sulfuric acid, sulfuric anhydride or the like having a concentration above 90% by weight can be used. If the concentration of sulfuric acid to be added to the reaction system is below 90% by weight, it is not economical because the quantity of the use of sulfuric acid increases.

The quantity of sulfuric acid used in this step is generally 1 to 10 times, preferably 2 to 8 times the moles of acetaldehyde. If the quantity of sulfuric acid is less than the above range, the reaction does not proceed effectively and the formation of polymers increases. On the other hand, if the quantity of sulfuric acid exceeds the above range, it is not economical. The sulfuric acid used can be used again by adjusting it to a desired concentration after the use.

As the acetaldehyde used in the BBE preparation step, paraldehyde and acetaldehyde hydrate can also be used.

When this step is carried out with a concentration of acetaldehyde not higher than 1% by weight in the reaction system, a desirable result can be obtained. If the concentration of acetaldehyde exceeds 1% by weight, the formation of an intermediate, 1-(p-isobutylphenyl)ethanol increases. Furthermore, not only the side reaction such as polymerization increases but also the purity of used sulfuric acid becomes lower and it becomes difficult to recover and recycle the sulfuric acid.

The IBB used in this step is preferably those diluted by an inert solvent such as hexane, pentane or other aliphatic hydrocarbon. Recovered IBB of the succeeding step (I) or a mixture of them can also be preferably used, not to speak of pure IBB. The IBB is generally added in excess with regard to acetaldehyde and the addition quantity of IBB is 2 times or more, and preferably 2.2 times or more relative to the moles of acetaldehyde. If the quantity of IBB is less than the above value, the reaction does not proceed effectively and polymers are formed. More desirable results can be expected by using much IBB; however, the quantity to be treated increases as such. Therefore, the upper limit of use quantity of IBB must be determined in an economical viewpoint, and the maximum quantity is generally 100 times, preferably 20 times the moles of acetaldehyde.

The reaction must be carried out with stirring at temperatures not higher than 40° C., and preferably −20° to 20° C. If the reaction temperature is higher than 40° C., it is not desirable because side reactions of polymerization and the sulfonation of IBB abruptly increase. It is, therefore, desirable that the reaction vessel is cooled externally or internally.

In a preferable mode of this step, a mixture of IBB and sulfuric acid in a predetermined concentration are fed into a reaction vessel, and a predetermined quantity of acetaldehyde or its solution in IBB is added little by little for more than 2 hours. At the same time, sulfuric acid of a concentration higher than the concentration of the sulfuric acid aqueous solution in the reaction system, is added into the reaction mixture so as to maintain the concentration of the sulfuric acid aqueous solution in the reaction system above the preferable value of 75% by weight.

If the acetaldehyde or its IBB solution is added rapidly within a time shorter than 2 hours, the concentration of acetaldehyde in the reaction mixture increases to cause the formation of polymers. A long reaction time is, however, not necessary because the rate of reaction according to the invention is relatively high. Desirable reaction times are 3 to 10 hours.

There is no limit with respect to reaction pressures, however, the reaction is preferably done at the atmospheric pressure or at the equilibrated pressure within a sealed reaction vessel at respective reaction temperatures.

After the reaction, stirring is stopped and the reaction mixture is then allowed to stand in the same reaction vessel or in a settling tank by transferring the reaction mixture into the tank. The lower layer is a sulfuric acid aqueous layer which contains the most of dissolved sulfonation product of IBB that was produced by the side reaction in sulfonation. This sulfuric acid layer is recovered and the concentration of the sulfuric acid is adjusted to a certain level, which can be used again. Contained in the upper hydrocarbon layer are BBE, unreacted IBB and the most of by-product hydrocarbons. This upper layer is separated and remaining sulfuric acid is neutralized with an alkaline substance such as NaOH, KOH, $Ca(OH)_2$ or $Na_2CO_3$ or their aqueous solutions, and then it is rinsed with water.

In this step, it is possible to add a solvent such as ether or n-hexane in order to avoid emulsifying that is caused by sulfonated products.

After the neutralization, the hydrocarbon layer is distilled preferably under a reduced pressure to obtain the unreacted IBB and the product, BBE. In the present invention, because the isomerization of IBB as the unreacted material does not occur at all, the IBB recovered by ordinary distillation can be used again by recycling it without applying any special refining treatment. The obtained BBE is a new compound in which isobutyl groups are introduced at the p-positions. Therefore, the BBE is symmetrical and it is desirable as the starting compound that is used for the next catalytic cracking step (I).

In the first step (I) of the invention, the BBE is subjected to catalytic cracking in the presence of a protonic acid catalyst, solid acid catalyst or protonic acid-carrying solid acid catalyst to produce p-isobutylstyrene (PBS) and IBB which is the starting material in the said BBE preparation step.

The temperatures in the catalytic cracking can be selected within the range of 200° to 650° C. according to the kind of catalyst and the mode of reaction such as gaseous phase or liquid phase.

As catalysts for the catalytic cracking, inorganic protonic acids including phosphoric acid, sulfuric acid, hydrochloric acid and heteropoly acids such as silicotungstic acid and organic protonic acids such as p-toluene sulfonic acid are preferable. Furthermore, several solid acids such as silica, alumina, synthetic siliceous catalysts such as silica-alumina, silica-magnesia and synthetic zeolite; silica-alumina clay catalysts such as kaolin, attapulgite, acid clay and fuller's earth which are produced from natural clay minerals; and catalyst-carrying solid acids which carries the foregoing protonic acids on them, can also be desirably used. On the other hand, the so-called Lewis acid catalysts of non-protonic acids that are typically exemplified by halogenated metals such as boron fluoride, aluminum chloride, iron chloride, iron bromide and zinc chloride are not desirable because isobutyl groups are isomerized into sec-butyl groups or the like and the polymerization of produced PBS occurs in the catalytic cracking.

The catalytic cracking can be carried out in any of gaseous phase and liquid phase; however, the cracking in a liquid phase with a protonic acid catalyst or the cracking in a gaseous phase with the foregoing protonic acid-carrying solid acid catalyst are preferable. Especially, in view of the prevention of corrosion of reaction apparatus and the adoption of continuous reaction system, the vapor phase catalytic cracking with a solid acid catalyst is preferable.

In the liquid phase catalytic cracking in the presence of a protonic acid catalyst, the reaction temperatures are preferably in the range of 200° to 350° C. and more preferably 250° to 325° C. If the reaction temperature is higher than the above range, side reaction increases and selectivity becomes worse. On the other hand, if the reaction temperature is lower than the above range, the rate of reaction is low which is not desirable in an economical viewpoint.

The quantity of the protonic acid used in the liquid phase catalytic cracking in step (I) is in the range of 0.001 to 100 times the moles of BBE, and preferably 0.005 to 10 times. If the quantity of the protonic acid is smaller than the above range, the conversion ratio of BBE is too low. Meanwhile, if the quantity of the protonic acid is larger than the above range, there occurs no objectionable matter, however, it is not desirable in an economical viewpoint.

The protonic acids used in the above process are exemplified by inorganic acids such as phosphoric acid, sulfuric acid, and heteropoly acids of phosphotungstic acid and silicotungstic acid; and organic sulfonic acids such as p-toluenesulfonic acid and naphthalenesulfonic acid. Among them, the phosphoric acid is especially preferable because of its good efficiency. As the phosphoric acid, any of orthophosphoric acid, pyrophosphoric acid, polyphosphoric acid and metaphosphoric acid can be used.

In the process of the invention, commercially available acids as they stand can be used or they can also be used in the form of aqueous solutions.

There is no limit with regard to the pressure in the reaction as far as the produced PBS and IBB can be vaporized under predetermined reaction conditions. The reaction is, however, preferably carried out under atmospheric pressure or reduced pressure.

The contact time between the fed material BBE and the catalyst can be properly selected, wherein 0.001 to 1000 hr.g.cat/g is preferable, and 0.01 to 100 hr.g.cat/g is more preferable.

As the catalysts used in the vapor phase catalytic cracking are exemplified by solid acids such as silica, alumina, synthetic siliceous solid acid catalysts such as silica-alumina and silica-magnesia and zeolite type catalysts such as synthetic zeolite; and clay solid acid catalysts such as kaolin, attapulgite, acid clay and fuller's earth which are produced from natural clay minerals. As the catalyst-carrying solid acids are exemplified by those which carries the foregoing protonic acids on the above solid acids. These catalyst-carrying solid acids are prepared by the conventional methods, for example, a solid acid is impregnated with an aqueous solution of protonic acid and it is then dried.

The reaction pressure in the vapor phase catalytic cracking using the solid acid or catalyst-carrying solid acid may be any of atmospheric, elevated and reduced pressures as far as the reaction gases can be maintained in a gaseous phase under a predetermined reaction temperature. Furthermore, the object of the invention can be attained by any of fixed bed process, moving bed process and fluidized bed process. Still further, it is desirable to use a catalyst having a surface area of a certain level. For example, the surface area of the solid acid may be not smaller than 250 m$^2$/g and preferably 350 to 1000 m$^2$/g. If a catalyst of a smaller surface area is used, the ratio of conversion is sometimes lowered as compared with the case in which a catalyst having a larger surface area is used.

The contact time between the reactant gas and the solid acid catalyst is generally in the range of 0.05 to 5 seconds. However, it can be determined more freely according to the composition of reactant gas, kind of solid acid catalyst, reaction temperature and preheating temperature of reactant gases.

The reaction temperatures are preferably in the range of 300° to 650° C. and more preferably 350° to 500° C. If the reaction temperature is higher than the above range, side reaction increases and selectivity becomes worse. On the other hand, if the reaction temperature is lower than the above range, the rate of cracking is low which is undesirable in an economical viewpoint.

In any of gas phase cracking and liquid phase cracking the reaction product can be diluted or mixed with an inert gas for the purpose of distilling off the produced PBS rapidly and preventing the catalyst from deterioration. The inert gases used for the above purposes are exemplified by hydrogen, nitrogen, helium, methane, mixtures of these gases and steam.

Especially in the gas phase cracking, it is preferable that the reaction is done in the presence of steam in order to improve the yield of PBS by suppressing the formation of p-isobutylethylbenzene (PBE). The quantity of steam is 2 times or more the weight of BBE and preferably 4 times or more. The maximum quantity of the steam to coexist is not limited, however, it is preferable that the steam is not more than 100 times the weight of BBE from an economical viewpoint.

The BBE used in the step (I) of catalytic cracking is a symmetrical diarylalkane. Owing to this fact, cracking products produced in step (I) are mainly IBB, i.e. the starting material of the said BBE preparation step, and PBS which is the starting material of the next step (II) or (III); and small quantities of side reaction products in which the vinyl groups of PBS are saturated such as p-isobutyl ethylbenzene, though the formation of side reaction products depends upon the kind of catalyst used. When asymmetrical diarylalkanes are cracked, the PBS and IBB as those in the method of the present invention cannot be obtained and, even when they are produced, many other cracking products which are difficultly separated are formed. Therefore, in the present invention, the stable PBS as well as IBB can be recovered in a sufficiently pure form by easier refining process such as simple distillation. The recovered IBB can be used either being recycled to the BBE preparation step in a continuous process or being recycled after once held in a storage tank in a batchwise process. Accordingly, because at least a part of recovered IBB is recycled to produce BBE by reaction with acetaldehyde in the presence of sulfuric acid, the present invention can be made more advantageous in an economical viewpoint. Furthermore, the PBS can be used for the material of succeeding carbonylation step (II) or (III). These facts are quite important for carrying out the method of the present invention economically at low cost.

In the following, the BBE preparation step and the step (I) of the present invention will be described in more detail with reference to the accompanying drawing.

In the first place, IBB, acetaldehyde and sulfuric acid are fed into a reaction vessel 1. A portion of the IBB is fed from a line 18 as a recycled IBB. After the reaction, the contents are transferred to a settling vessel 2 through a line 11. In the settling vessel 2, the lower layer of sulfuric acid is separated and the upper layer is then transferred into a neutralizing vessel 3 in which the remaining sulfuric acid is neutralized and the neutralized product is then fed into a distillation column 4.

In this distillation column 4, unreacted IBB and BBE are separated. The recovered IBB is returned to the reaction vessel 1 through lines 16 and 18. The BBE separated in the distillation column 4 is then subjected to catalytic cracking in a cracking vessel 5 and the cracking product is then fed into another distillation column 6 through a line 14. In the distillation column 6, PBS and IBB are separated. The PBS is recovered from a line 15 and the separated IBB is recycled to the reaction vessel 1 through lines 17 and 18.

In the step (II) as the second stage according to the the present invention, the carbonylation of PBS that is obtained in the preceding step (I) is done to obtain IPA or its ester of IPE.

This step can be carried out in accordance with the conventional method in which olefinic unsaturated compound is reacted with alcohol or water and carbon monoxide in the presence of a metal complex carbonylation catalyst.

When water is used, IPA is obtained, and when an alcohol is used, a corresponding ester of IPA is obtained. As the metal complex carbonylation catalysts, there are exemplified metal complexes of precious metals such as Pd, Rh, Ir, Pt and Ru; and Ni, Co and Fe. With regard to the oxidation number of precious metals, any of those of zero to the maximum oxidation number can be used and metal complexes having ligands of halogen atoms, trivalent phosphorus compounds, $\pi$-allyl groups, amines, nitriles, oximes, olefins and carbon monoxide are effective.

The metal complex carbonylation catalysts are exemplified by bistriphenylphosphine dichlorocomplex, bistributylphosphine dichlorocomplex, bistricyclohexylphosphine dichlorocomplex, $\pi$-allyltriphnenylphosphine dichlorocomplex, triphnenylphosphine piperidine dichlorocomplex, bisbenzonitrile dichlorocomplex, biscyclohexyloxime dichlorocomplex, 1,5,9-cyclododecatriene dichlorocomplex, bistriphenylphosphine dicarbonyl complex, bistriphenylphosphine diacetate complex, bistriphenylphosphine dinitrate complex, bistriphenylphosphine sulfate complex, tetrakistriphenylphosphine complex; and complexes in which a part of ligands are carbon monoxide such as chlorocarbonyl bistriphenylphosphine complex, hydridocarbonyl tristriphenylphosphine, bischlorotetracarbonyl complex and dicarbonyl acetylacetonate complex, of the above-mentioned metals.

Furthermore, compounds which produces the above metal complexes in the reaction system can be also used. That is, phosphine, nitrile, allyl compound, amine, oxime, olefin or carbon monoxide which is able to be the ligands to the oxides, sulfates or chlorides of the above precious metals or else, are simultaneously added into the reaction system in the carbonylation reaction.

The above phosphines are exemplified by triphenylphosphine, tritolylphosphine, tributylphosphine, tircyclohexylphosphine and triethylphosphine. The nitriles are exemplified by benzonitrile, acrylonitrile, propionitrile and benzylnitrile. The allyl compounds are exemplified by allyl chloride and allyl alcohol. The amines are exemplified by benzylamine, pyridine, piperazine and tri-n-butylamine. The oximes are exemplified by cyclohexyloxime, acetoxime and benzaldoxime. The olefins are exemplified by 1,5-cyclooctadiene and 1,5,9-cyclododecatriene.

The alcohols used in this step are lower aliphatic alcohols having 1 to 4 carbon atoms such as methanol, ethanol, propanol and butanol. When higher alcohols than the above ones are used, the boiling point of produced IPE becomes too high, which is undesirable because the refining of IPE is difficult.

The quantity of a metal complex or a compound which produces a metal complex to be used in this step as a catalyst is 0.0001 to 0.5 mole, preferably 0.001 to 0.1 mole to one mole of PBS. When the compound which produces a metal complex is used, the addition quantity of the compound to form ligands is 0.8 to 10 moles, preferably 1 to 4 moles to one mole of the compound to produce a metal complex.

Alcohol and water act as solvents as well as the reactants. The use quantities of them are 0.5 to 50 parts by weight and preferably 1 to 20 parts by weight to one part by weight of PBS.

Furthermore, for the purpose of improving the rate of reaction, it is possible to add inorganic halides such as hydrogen chloride and boron trifluoride, or organic iodide such as methyl iodide.

When these halides are added, the quantities of them are 0.1 to 30 moles, preferably 1 to 15 moles as halogen atoms to 1 mole of the complex catalyst or the compound to produce a complex. Even though it depends upon the kind of catalyst, if the addition quantity is less than 0.1 mole, the effect of the addition cannot be observed sometimes. If the addition quantity exceeds 30 times by moles, not only the catalytic activity is lowered but also halogen atoms are added to the double bonds of PBS which fact becomes a bar to the aimed reaction.

It is only necessary that the quantity of carbon monoxide to be fed is excess relative to the quantity of PBS. Even though it depends upon the size and form of a reaction vessel, the termination of reaction can be confirmed generally by observing the phenomenon that the absorption of carbon monoxide that exists in the reaction vessel under pressure is ceased and the lowering of the pressure within the reaction vessel is also ceased.

The carbonylation reaction is carried out at temperatures in the range of 40° to 150° C., preferably 60° to 110° C. and at a carbon monoxide pressure in the range of 30 to 400 kg/cm$^2$. If the reaction temperature is below 40° C., the rate of reaction is very low which is not acceptable in industrial production process. On the other hand, if the reaction temperature is above 150° C., it is not desirable because side reactions of polymerization and decomposition of complex catalyst are caused to occur. Also, if the pressure of carbon monoxide is lower than 30 kg/cm$^2$, the reaction rate is so slow that the reaction cannot be carried out practically. The upper limit of the pressure is not restricted but in a practical viewpoint, it is desirable that the pressure is not higher than 400 kg/cm$^2$. It is sufficient that the reaction is continued until the lowering of pressure owing to the absorption of carbon monoxide is stopped. When the carbonylation is carried using water as a solvent, the IPA is produced. While, by using an alcohol as a solvent, an alkyl ester of IPA, i.e. IPE which has the ester moiety of the alkyl group of the alcohol, can be easily obtained. Because the IPE obtained in the presence of alcoholic solvent is stable, the IPE can be refined easily by simple distillation or the like. Furthermore, the final product of $\alpha$-(p-isobutylphenyl) propionic acid can be easily obtained by the convention method of hydrolysis of esters. For example, the IPE is refluxed with an aqueous solution of sodium hydroxide and the precipitate of the acid, IPA, is separated and recrystallized in n-hexane or petroleum ether. The thus obtained $\alpha$-(p-isobutylphenyl)-propionic acid is very pure.

It is possible to use again the metal complex catalyst that is recovered after the reaction.

In place of the foregoing step (II), the step (III) can be carried out as a second stage. In the step (III), PBS is reacted with hydrogen and carbon monoxide in the presence of a metal complex carbonylation catalyst to obtain IPN and it is then oxidized to produce IPA.

The kinds, quantities and manner of use of the metal complex carbonylation catalysts will not be described here repeatedly because they are just the same as those in the foregoing step (II). Furthermore, it is also the same that inorganic halides and organic iodides can be added in order to improve the rate of reaction.

The carbonylation reaction in the step (III) is carried out at temperatures in the range of 40° to 150° C., preferably 55° to 110° C. If the reaction temperature is below 40° C., the rate of reaction is very low which is not acceptable in industrial production process. On the other hand, if the reaction temperature is above 150° C., it is not desirable because side reactions of polymerization and addition of hydrogen, and decomposition of complex catalyst are caused to occur.

The pressure of reaction may be properly determined as far as it is above 5 kg/cm². If the reaction pressure is lower than 5 kg/cm², the rate of reaction is so low that the reaction cannot be carried out practically. If the reaction pressure is high enough, the reaction will proceed faster, however, a too high pressure requires highly pressure resistant reaction apparatus, which will determined the upper limit of reaction pressure. It is thus practically sufficient that the reaction pressure is set at a level lower than 500 kg/cm².

The reaction is continued until the lowering of pressure owing to the absorption of the mixed gas of carbon monoxide and hydrogen, is not observed. The reaction time of 4 to 20 hours is generally sufficient.

The carbon monoxide and hydrogen that are necessary for the reaction can be fed either separately or by mixing them previously. The molar ratio of carbon monoxide and hydrogen to be fed into the reaction system can be selected arbitrary. In this carbonylation reaction of the step (III) of the invention, carbon monoxide and hydrogen are consumed (absorbed) accurately at a molar ratio of 1:1. Accordingly, as the gas supplied in excess remains unreacted, the reaction is proceeded again if the other gas is supplied at the time when the lowering of pressure is ceased and reactants still remain. Even though it will depend upon the size of reaction vessel and the mode of reaction, it is generally most effective that carbon monoxide and hydrogen are fed in a molar ratio of 1:1.

In the carbonylation of this step of the invention, it is possible in order to remove the heat of reaction to use a solvent which is inert to the carbonylation. Exemplified as the solvents that are inert to carbonylation are polar solvents such as ethers, ketones and alcohols, and nonpolar solvents such as paraffins, cycloparaffins and aromatic hydrocarbons. However, satisfactory result can be obtained generally in the condition without any solvent.

The thus obtained reaction product is then distilled under a reduced pressure to separate IPN and the catalyst quite easily. The recovered complex catalyst can be used again for the next carbonylation reaction.

In this step of the invention, the carbonylation is carried out by using the stable and highly pure PBS that is obtained in the step (I). Accordingly, the obtained IPN contains only a small quantity of β-(p-isobutylphenyl)propionaldehde propionaldehyde (NPN) and it can be easily refined to produce highly pure IPN.

Because IPN can be prepared in a very pure form by the method of the invention, α-(p-isobutylphenyl)propionic acid (IPA) can be easily obtained by oxidizing the IPN.

The oxidation is carried out under relatively moderate conditions because IPN has an aldehyde group and a hydrogen atom on α-position. For example, IPN is oxidized by a mild oxidizing agent of an aqueous solution of potassium permanganate, an aqueous alkaline suspension of silver oxide or bromine water. Especially preferable oxidizing method is to oxidize with a hypohalogenous acid under an acidic condition. The hypohalogenous acid are exemplified by sodium, potassium and calcium salts of hypochlorous acid or hypobromous acid. It is desirable that the oxidation is performed with cooling at temperatures in the range of $-10°$ to $30°$ C.

In the BBE preparation step, because IBB is reacted with acetaldehyde in the presence of sulfuric acid catalyst, the isomerization of isobutyl groups is not caused to occur. In addition, a novel compound of BBE is obtained with a good selectivity to p-position. Accordingly, the unreacted IBB can be recovered effectively and the yield of BBE is quite good.

In the step (I), a new compound of symmetrical diarylalkane of BBE is catalytically cracked. Because such the symmetrical diarylalkane is cracked, the main cracking products are PBS and IBB. The IBB can be used again as a starting material in the BBE preparation step, which fact makes the method of the invention valuable in an economical viewpoint.

Because protonic acids and solid acids are used as catalysts of catalytic cracking, the isomerization of isobutyl groups and polymerization of PBS do not occur. Therefore, IBB and PBS can be obtained in higher yields. Furthermore, as the by-products in cracking can be easily separated off and the obtained PBS is stable, the refining can be easily done to obtain PBS and IBB.

The highly pure PBS obtained in the step (I) is then carbonylated in the succeeding step (II) or (III) to produce IPA, IPE or IPN. In the carbonylation of PBS, highly pure products scarcely containing impurities can be obtained. The IPE obtained with the solvent of alcohol can be easily hydrolyzed into IPA, meanwhile, the IPA is directly produced when water is used as a solvent. The IPN is also easily converted into IPA by oxidation.

As described above, in the method of the present invention, isobutylbenzene (IBB), acetaldehyde, sulfuric acid, carbon monoxide and alcohols such as methanol, ethanol, propanol and butanol that are safe, stable, industrially easily available and inexpensive are used without requiring any special handling. The final aimed product of α-(p-isobutylphenyl)propionic acid (IPA) or its ester of α-(p-isobutylphenyl)propionic ester (IPE) can be obtained by simple operation from the above materials through only three steps of processes by obtaining an intermediate product that is stable and easily refined industrially. Accordingly, the present invention provides an easy and economical method of production in an industrial scale.

In other words, the method for producing IPA or its ester of IPE has been accomplished by turning attention to the new compound of BBE and by using more inexpensive materials as compared with those in the conventional method and by employing a simple and easily handled intermediate compound, BBE. Therefore, the method of the present invention can be said to be epochal.

In the following, the present invention will be described in more detail with reference to several examples.

BBE Preparation Step

EXAMPLE 1

To a 2 liter round bottom flask with a stirrer were fed 402 g (3 moles) of IBB and 600 g (5.8 moles) of 95 wt.% sulfuric acid and it was maintained below 10° C. by external ice-cooling. A mixture of 44 g (1 mole) of acetaldehyde and 67 g (0.5 mole) of IBB was added dropwise gradually for 4 hours with stirring. The reaction temperature was maintained below 10° C. After the dropwise addition, stirring was continued for further 2 hours. After the reaction, the reaction mixture was transferred into a separating funnel and allowed to stand still.

The lower sulfuric acid layer was removed and about 2% NaOH aqueous solution was added with shaking until the content was neutralized. The lower water layer was then discharged and the oily layer was put into a still and it was refined by distillation under a reduced pressure to obtain 260 g of BBE having the following properties. The yield of BBE was 88% by mole on the basis of acetaldehyde. The BBE prepared like the above procedure was used in examples of the succeeding step (I).

Incidentally, the concentration of acetaldehyde in the reaction mixture during the addition of the acetaldehyde solution was not higher than 0.5% by weight and the concentration of sulfuric acid in the sulfuric acid layer after the reaction was 93% by weight.

Furthermore, the fraction of the boiling range of 60° to 80° C. at 3 mmHg was analyzed by gas-liquid chromatography (GLC) and nuclear magnetic resonance (NMR). As a result, it was understood that the fraction was just the same substance as the IBB that was used as the starting material.

| Properties of BBE: | | |
|---|---|---|
| Boiling Point: | 180–183° C./3 mmHg (colorless liquid) | |
| Infrared Absorption Spectrum Analysis: (Liquid-film method) | | |
| $2960 \text{ cm}^{-1}$, $1540 \text{ cm}^{-1}$, | $1480 \text{ cm}^{-1}$, | $1390 \text{ cm}^{-1}$ |
| $1370 \text{ cm}^{-1}$, $1210 \text{ cm}^{-1}$, | $850 \text{ cm}^{-1}$, | $800 \text{ cm}^{-1}$ |
| Nuclear Magnetic Resonance Spectrum Analysis: ($CCl_4$ solvent, δ ppm) | | |
| 6.95 | (8H Singlet) | |
| 3.7–4.2 | (1H Quadruplet) | |
| 2.39 | (4H Doublet) | |
| 1.58 | (3H Doublet) | |
| 0.87 | (12H Doublet) | |
| 1.6–2.2 | (2H Multiplet) | |
| Mass Spectrum Analysis: (EI. 70 eV) | | |
| m/e | Pattern Coefficient | |
| 294 | (29) | |
| 279 | (100) | |
| 251 | (21) | |
| 237 | (19) | |
| 193 | (33) | |
| 91 | (30) | |
| Elemental Analysis: (as $C_{22}H_{30}$) | | |
| Calculated: | C: 89.80 | H: 10.20 |
| Found: | C: 89.83 | H: 10.06 |

EXAMPLES 2 to 4

IBB and acetaldehyde were reacted in the like manner as Example 1 except that the molar ratios of them were varied and BBE was obtained. The results are shown in the following Table 1.

EXAMPLE 5 to 8

IBB and acetaldehyde were reacted in the like manner as Example 1 except that the concentration of sulfuric acid were varied and BBE was obtained. The results are shown in the following Table 1.

TABLE 1

| | Feeds to Flask | | Additives | | Results | |
|---|---|---|---|---|---|---|
| Example Number | IBB g (mole) | Sulfuric Acid, g (Conc. wt %) | IBB g (mole) | Acetaldehyde g (mole) | Yield of BBE (%) | Conc. of Sulfuric Acid (wt %) |
| 2 | 230 (1.7) | 600 (95) | 67 (0.5) | 44 (1) | 75 | 93 |
| 3 | 670 (5) | 600 (95) | 67 (0.5) | 44 (1) | 93 | 92 |
| 4 | 134 (1.0) | 600 (95) | 67 (0.5) | 44 (1) | 45 | 94 |
| 5 | 402 (3) | 600 (90) | 67 (0.5) | 44 (1) | 90 | 87 |
| 6 | 402 (3) | 600 (87) | 67 (0.5) | 44 (1) | 77 | 85 |
| 7 | 402 (3) | 600 (83) | 67 (0.5) | 44 (1) | 74 | 81 |
| 8 | 402 (3) | 600 (75) | 67 (0.5) | 44 (1) | 30 | 75 |

EXAMPLE 9

To a 2 liter round bottom flask with a stirrer were fed 402 g (3 moles) of IBB and 600 g (5.8 moles) of 95% wt. % sulfuric acid and it was maintained below 10° C. by external ice-cooling. A mixture of 44 g (1 mole) of acetaldehyde and 67 g (0.5 mole) of IBB was slowly added dropwise for 4 hours with stirring. At the same time, 100 g (1 mole) of 98 wt. % sulfuric acid was also slowly added dropwise for 4 hours. The reaction temperature was maintained below 10° C. After the dropwise addition, stirring was continued for further 2 hours.

After the reaction, the reaction mixture was transferred into a separating funnel and allowed to stand still. The lower sulfuric acid layer was then removed and about 2% NaOH aqueous solution was added with shaking until the contents were neutralized. The lower water layer was then discharged and the oily layer was put into a still and it was refined by distillation under a reduced pressure to obtain BBE in a yield of 89% on the basis of acetaldehyde Incidentally, the concentration of acetaldehyde in the reaction mixture during the addition of the acetaldehyde solution was not higher than 0.5% by weight and the concentration of sulfuric acid after the reaction was 95% by weight.

EXAMPLE 10

To a 2 liter round bottom flask with stirrer were fed 402 g (3 moles) of IBB and 400 g (3.5 moles) of 85 wt. % sulfuric acid and it was maintained below 10° C. by external ice-cooling. A mixture of 44 g (1 mole) of acetaldehyde and 67 g (0.5 mole) of IBB was slowly added dropwise for 4 hours with stirring. At the same time, 150 g of 30% fuming sulfuric acid was added dropwise for 4 hours. The reaction temperature was maintained below 10° C. After the dropwise addition, stirring was continued for further 2 hours.

After the reaction, BBE was obtained in the like manner as Example 1. The yield of BBE was 87% on the basis of acetaldehyde. The concentration of the sulfuric acid after the reaction was 88 wt. %.

COMPARATIVE EXAMPLES 1 to 6

In place of producing BBE from IBB and acetaldehyde using sulfuric acid, the sulfuric acid as a catalyst and the alkylating agent for IBB were replaced by the substances as shown in the following Table 2. Other conditions were made the same as those in the foregoing Example 1. The quantity of alkylating agent for IBB was 0.2 mole in all tests.

The results are shown also in the same Table 2, which indicates that it is impossible to prepare BBE in a good yield with a good selectivity. Accordingly, it will be understood that it is most economical to react acetaldehyde in the presence of sulfuric acid when IBB is used as a starting material in the BBE preparation step.

TABLE 2

| Comparative Example Number | Alkylating Agent | Catalysts | Reaction Conditions | Result Yield (%) | p-Position Selectivity (%) |
| --- | --- | --- | --- | --- | --- |
| 1 | Acetaldehyde | Phosphoric acid/BF3 | 50° C./6 hours | 3 | — |
| 2 | Acetaldehyde | Phosphoric acid | 50° C./6 hours | 0 | — |
| 3 | 1,1-Dichloroethane | Anhyd. aluminum chloride | 5° C./4 hours | 20 | 66 |
| 4 | 1,1-Dichloroethane | BF3 | 20° C./4 hours | 2 | — |
| 5 | Vinyl chloride | Anhyd. aluminum chloride | 5° C./4 hours | 3 | — |
| 6 | Acetylene | Sulfuric acid/ Silver sulfate | 15° C./5 hours | 35 | 30 |

Step (I)

Preparation of p-isobutylstyrene (PBS) and isobutylbenzene (IBB) by the cracking of 1,1-bis(p-isobutylphenyl)ethane (BBE)

EXAMPLE 11

A 500 ml reaction vessel was equipped with a condenser, a sitirrer and a gas feeding device. To this reaction vessel were added 148 g (0.5 mole) of BBE that obtained in Example 1 and 50 g (0.02 mole) of silicotungstic acid as a catalyst. BBE was cracked by heating the reaction mixture to 280° C. When temperature is raised to above 200° C., 1 liter/min. of hydrogen was fed from the gas feeding device and the gas together with cracking products were introduced into the condenser to collect the cracking products. This cracking was continued until the effluent was ceased.

According to GLC analysis of the effluent, it contained 7% of p-isobutylethylbenzene (PBE) (a compound formed by hydrogenating the double bond of PBS), 47% of IBB and 39% of PBS and 6% of the starting material BBE.

Each component was then separated and was analyzed by mass spectrum, IR and NMR. As a result, it was confirmed that the IBB and BBE were just the same as those used as starting materials and the side reactions such as the isomerization of isobutyl groups did not occur. Furthermore, in accordance with the analytical results on PBE and PBS, the butyl groups were isobutyl groups and the position of substitution was p-position.

EXAMPLES 12 TO 16 AND COMPARATIVE EXAMPLE 7

In the like manner as Example 11, catalytic cracking was carried out by changing the catalyst. The results are shown in the following Table 3.

TABLE 3

| Example Number | Catalyst | Introduced Gas | Composition of Distillate (wt. %) | | | |
| --- | --- | --- | --- | --- | --- | --- |
| | | | IBB | PBE | PBS | BBE |
| 12 | Phosphoric acid | Nitrogen | 46 | 9 | 34 | 5 |
| 13 | Sulfuric acid | Nitrogen | 45 | 12 | 33 | 8 |
| 14 | Naphthalene sulfonic acid | Hydrogen | 44 | 7 | 38 | 8 |
| 15 | Toluene sulfonic acid | Hydrogen | 38 | 7 | 29 | 11 |
| 16 | Phosphotungstic acid | Nitrogen | 45 | 8 | 37 | 6 |
| Comp. Ex. 7 | Anhyd. aluminum chloride | Hydrogen | (*) See Note below | | | |

Note: (*) According to GLC analysis, the distillate contained only the components that were lighter than IBB. Furthermore, a large quantity of sticky substance remained in the reaction vessel.

EXAMPLE 17

A synthetic silica-alumina type catalyst FCC-HA (trademark, made by Catalyst & Chemical Industries Co., Ltd. ) was granulated to a particle diameter of 0.5 to 1 mm. This catalyst (5 ml) was filled in a stainless steel tube of 60 cm in length and 10 mm in inner diameter. Cracking was carried out by feeding 5 ml/hr of BBE obtained in Example 1, 200 ml/min of hydrogen and 30 ml/hr of water through a preheating tube at 450° C. into the catalyst bed. The cracking products were ice-cooled and gas and liquid were separated from each other. The organic layer above water was distilled and the fractions of IBB and PBS were recovered, respectively. With respect to the organic layer, the ratio of cracking and selectivity were determined by GLC analysis.

The composition of the cracked product was 30 wt. % of IBB, 6 wt. % of PBE, 26 wt. % of PBS, 37 wt. % of BBE and 1 wt. % of unknown substance. It was thus confirmed that the selectivity in the cracking was high. The structural analysis was done with regard to each component in the like manner as Example 11 and it was confirmed that the isobutyl groups were not isomerized and the selectivity to p-position of cracked product was high.

In order to confirm that the above obtained IBB can be used by recycling it as the starting material IBB in the BBE preparation step, preparation of BBE was carried out in the like manner as Example 1 except that the IBB obtained in the above procedure was used as the starting IBB. With respect to the yield and purity of the obtained BBE were almost the same as those of the foregoing Example 1.

EXAMPLES 18 TO 27

Using solid acids in place of the FCC-HA catalyst, the BBE obtained in Example 1 was catalytically cracked in the like manner as Example 17. The results are shown in the following Table 4.

TABLE 4

| Example Number | Catalyst | Results | |
|---|---|---|---|
| | | Ratio of Cracking (wt. %) | Ratio of PBS/PBE |
| | *Clay type solid acid* | | |
| 18 | Kaolin Clay (Engelhard Corp.) | 55 | 8.0 |
| 19 | Activated Caly (Nippon Kassei Hakudo Co., Ltd.) | 25 | 5.1 |
| 20 | Galleonite #036 (Mizusawa Industrial Chemicals, Ltd.) | 15 | 3.8 |
| 21 | Attapulgus Clay (Engelhard Corp.) | 30 | 4.2 |
| | *Synthetic type silica-alumina solid acid* | | |
| 22 | IS-28 (Catalyst & Chemical Industries Co., Ltd.) | 72 | 6.8 |
| 23 | FCC-HA (Catalyst & Chemical Industries Co., Ltd.) | 63 | 3.9 |
| 24 | FCC-LA (Catalyst & Chemical Industries Co., Ltd.) | 56 | 5.7 |
| | *Zeolite type solid acid* | | |
| 25 | SZ-C (Catalyst & Chemical Industries Co., Ltd.) | 65 | 5.3 |
| 26 | SZ-H (Catalyst & Chemical Industries Co., Ltd.) | 70 | 4.9 |
| 27 | MR-Z 230 (Catalyst & Chemical Industries Co., Ltd.) | 78 | 4.7 |

EXAMPLE 28

A silica gel (30 g, trademark Silbead N made by Mizusawa Industrial Chemicals, Ltd.) was added into 2 wt. % sulfuric acid aqueous solution and water was then removed and dried by heating it under a reduced pressure. The obtained sulfuric acid carrying-silica gel was granulated into a particle diameter of 0.5 to 1 mm and it was used as a cracking catalyst.

The cracking was carried out in the like manner as Example 17 at a cracking temperature of 300° C.

According to GLC analysis of the cracking products, the composition was 27 wt. % of IBB, 8 wt. % of PBE, 17 wt. % of PBS, 46 wt. % of BBE and 2 wt. % of unknown substance. The ratio of cracking was 53% by weight and the ratio of PBS/PBE was 2.1.

Synthesis and Cracking of Asymmetric Diarylalkane (To be Compared with the Invention)

REFERENCE EXAMPLE 1

Synthesis of Asymmetric Diarylalkane

To a 3 liter flask equipped with a stirrer were fed 670 g (5 moles) of IBB and 100 g of 95% sulfuric acid and it was cooled to 10° C. by ice-cooling. With maintaining the temperature at 10° C., a mixture of 134 g (1 mole) of IBB and 104 g (1 mole) of styrene was added dropwise for 4 hours. After the dropwise addition, the reaction was continued for further 1 hour.

After separating and removing the sulfuric acid layer, the remainder of the reaction mixture was neutralized and rinsed with water. It was then distilled under a reduced pressure of 3 mmHg to obtain 120 g of 1-(p-isobutylphenyl)1-phenylethane (hereinafter referred to as "PBPE").

REFERENCE EXAMPLE 2

Using 118 g (1 mole) of p-methylstyrene in place of the styrene, synthesis was carried out in the like manner as Reference Example 1 to obtain 80 g of 1-(p-isobutylphenyl)-1-(p-toyl)ethane (hereinaftere referred to as "PBTE").

COMPARATIVE EXAMPLE 8

Catalytic cracking was carried out in the like manner as Example 17 by using the PBPE and PBTE that are prepared in Reference Examples 1 and 2. In both the cases, the ratios of cracking were 55 to 60% by weight.

As shown in the following chemical formula, however, the ratio (A/B) of cracking product cleaved at the chain line A to the product cleaved at the chain line B was 8 to 9. In other words, most of the PBPE and PBTE were cleaved at the chain line A to produce the starting materials of styrene or p-methylstyrene rather than the aimed PBS. Accordingly, the yields of PBS were very low.

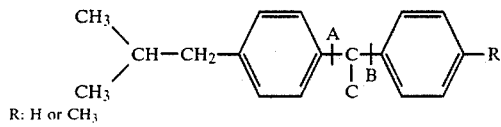

R: H or CH$_3$

The composition of the cracking product in the case of PBPE was as follows:

| | |
|---|---|
| Benzene | 2 % by weight |
| Ethylbenzene | 2 % by weight |
| Styrene | 17 % by weight |
| IBB | 20 % by weight |
| PBE | 1 % by weight |
| PBS | 2 % by weight |
| PBPE | 55 % by weight |

It will be understood from the above results that the ratio of cracking to PBS is low and, in order to recycle the IBB, complicated refining processes will be required.

Step (II)

Preparation of IPA or IPE by Carbonylation of PBS

EXAMPLE 29

To a 500 ml autoclave with a stirrer were fed 30 g of PBS obtained in Example 17, 200 ml of ethyl alcohol 1 g of bistriphenylphosphine dichloropalladium and 0.2 g of 30% boron trifluoride solution in ethyl ether. It was pressurized to 80 kg/cm$^2$ with carbon monoxide and reaction was carried out until the absorption of carbon monoxide was ceased.

After the reaction, the autoclave was cooled and unreacted gas was exhausted. By adding 1 g of potassium carbonate powder to the contents, a fraction of 90°-115° C./1 mmHg was obtained by simple distillation under reduced pressure, thereby separating the catalyst. According to the gas chromatographic analysis of this fraction, the composition thereof was 0.9 wt.

% PBE, 0.4 wt. % PBS, 93.7 wt. % IPE (ethyl ester) and 0.5 wt. % of ethyl ester of β-(p-isobutylphenyl)propionic acid (5 components).

The above fraction was distilled again under a reduced pressure to obtain 39 g of IPE (ethyl ester) of 118° to 121° C./1 mmHg. The purity of the product was 99.6% according to gas chromatographic analysis. Furthermore, the chemical structure of the product was confirmed by comparing with an authentic sample by IR analysis.

EXAMPLE 30

To a 500 ml autoclave were fed 30 g of PBS obtained in Example 17, 150 ml of 5% hydrogen chloride solution in methyl alcohol and 1 g of bisdichlorotriphenylphosphine palladium. It was pressurized to 300 kg/cm$^2$ at room temperature with carbon monoxide and, after heating to 90° C., it was pressurized further to 700 kg/cm$^2$ with carbon monoxide. The reaction was continued until the absorption of carbon monoxide was ceased.

After the reaction, the reaction product was treated in the like manner as Example 29 to obtain 23 g of IPE (ethyl ester) of the boiling point of 118° to 121° C./1 mmHg.

EXAMPLE 31

To a 500 ml autoclave were fed 30 g of PBS obtained in Example 17, 75 g of 10% hydrochloric acid aqueous solution 0.8 g of bisdichlorotriphenylphosphine palladium, 80 ml of benzene as a reaction solvent and 1 g of acetophenone. It was pressurized to 100 kg/cm$^2$ with carbon monoxide at room temperature. After heating it to 100° C., it was further pressurized to 300 kg/cm$^2$ with carbon monoxide and reaction was continued until the absorption of carbon monoxide was ceased.

After the reaction, the autoclave was cooled and benzene layer was separated and it was extracted three times with 50 ml of 5% aqueous solution of sodium hydroxide. Then hydrochloric acid was added until the sodium hydroxide solution became pH 2 and extracted with chloroform. The chloroform was removed by reduced pressure evaporation to obtain 37 g of light yellow crude crystal. This crude crystal was recrystallized with n-heptane to obtain a white crystal of IPA having a melting point of 76° to 77° C.. The recovery ratio by recrystallization was 78%. The maximum absorption of the ethanol solution of the white crystal in ultraviolet absorption was 220 mµ and, besides it, light absorption at 257 mµ, 263 mµ and 272 mµ was observed. Furthermore, it was confirmed by IR analysis that the obtained crystal was the same as the authentic sample.

EXAMPLE 32

Using 0.37 g of palladium chloride and 0.63 g of triphenylphosphine in place of the bisphenylphosphine dichloropalladium, reaction was carried out in the like manner as Example 29 and results similar to those of Example 29 were obtained.

EXAMPLE 33

Using 0.7 g of palladium dibenzylideneacetone and 1.2 g of diphenetyl neopentylphosphine in place of the bisphenylphosphine dichloropalladium, and 2 ml of trifluoroacetic acid in place of boron trifluoride ethyl ether solution, reaction was carried out in the like manner as Example 29 and 29 g of IPE (ethyl ester) of 99.3% purity was obtained.

REFERENCE EXAMPLE 3

Hydrolysis of Ethyl Ester

A mixture of 10 g of IPE (ethyl ester) obtained in Example 29 and 150 ml of 15% sodium hydroxide aqueous solution was prepared and hydrolysis of IPE was carried out at the refluxing temperature for 3 hours.

After cooling, oily content was extracted with ethyl ether and rinsed with water, and hydrochloric acid was added until the aqueous layer became pH 2. It was then extracted with carbon tetrachloride and the carbon tetrachloride was removed under a reduce pressure to obtain 8.2 g of light yellow crude crystal. The crude crystal was recrystallized with n-heptane to obtain 6.9 g of white crystal having a melting point of 75° to 76° C..

This crystal was compared with the authentic sample and as a result, it was understood that the crystal was the same IPA as that of Example 31.

Step (III)

Preparation of α-(p-isobutylphenyl)propionaldehyde (IPN) from p-isobutylstyrene (PBS)

EXAMPLE 34

To a 500 ml autoclave with a stirrer were fed 30 g of PBS obtained in Example 17 and 0.3 g of rhodium hydridocarbonyl tristriphenylphosphine. It was heated to 60° C. and pressurized to 50 kg/cm$^2$ with an equimolar gas mixture of hydrogen and carbon monoxide. The reaction was continued until the absorption of the mixed gas was ceased. After the reaction, the autoclave was cooled and the remaining mixed gas was exhausted. The contents were transferred into a simple distillation still and 34 g of crude IPN fraction of a distilling range of 60° to 90° C./2 mmHg was obtained. The composition of the obtained fraction was as follows:

| Composition of Crude IPN Fraction | |
|---|---|
| PBE | 0.3 % by weight |
| PBS | 0.1 % by weight |
| IPN | 89.9 % by weight |
| NPN | 9.7 % by weight |

This crude IPN fraction was treated again by reduced pressure distillation to obtain 27 g of IPN of a boiling range of 70° to 76° C./3 mmHg. The purity of this IPN was 99.6%.

OXIDATION

A flask with a thermometer, a condenser, a dropping funnel and a stirrer was fed with 19.03 g of IPN obtained in the above process, 80 ml of acetone and 9.0 g of acetic acid. The reaction was carried out by adding 68.8 g of sodium hypochlorite dropwise for 2 hours with cooling and stirring maintaining the temperature in the range of 5° to 15° C.. After the addition, the stirring was continued for further 1 hour.

The reaction mixture was then rinsed with water and extracted with benzene. The benzene layer was rinsed with water and neutralized with an aqueous solution of sodium hydroxide. It was then acidified by hydrochloric acid with cooling and it was further cooled to precipitate crystal. After recrystallization, IPA was obtained in a yield of 82%. The chemical structure of this was confirmed by comparing with an authentic sample.

EXAMPLE 35

Using 0.1 g of rhodium oxide and 0.6 g of triphenylphosphine in place of rhodium hydridocarbonyl tristriphenylphosphine, reaction was carried out in the like manner as Example 34. As a result, 31 g of crude IPN fraction containing 0.3 wt. % of PBE, 0.1 wt. % of PBS, 83.5 wt. % of IPN and 16.1 wt. % of NPN was obtained.

This crude IPN fraction was then oxidized in the like manner as Example 34 and IPA was obtained.

Hydroformylation

EXAMPLES 36 AND 37

In place of rhodium hydridocarbonyl tristriphenylphosphine, the complex catalysts shown in the following Table 5 was used and reaction was carried out in the like manner as Example 34 with a reaction temperature of 95° C. and a reaction pressure of 170 kg/cm$^2$.

The results are shown in the following Table 5.

TABLE 5

| Example Number | Catalyst | Crude IPN Fraction (g) | GLC Composition (wt. %) | | | |
|---|---|---|---|---|---|---|
| | | | PBE | PBS | IPN | NPN |
| 36 | IrCl(CO)(PPh$_3$)$_3$ | 24 | 3.1 | 0.7 | 75.7 | 20.5 |
| 37 | RuCl$_2$(PPh$_3$)$_2$ | 27 | 4.9 | 0.3 | 76.6 | 18.2 |

What is claimed is:

1. A method for producing α-(p-isobutylphenyl)-propionic acid or its alkyl esters which comprises the following steps of:
   (I) reacting isobutylbenzene and acetaldehyde in the presence of sulfuric acid to produce 1,1-bis(p-isobutylphenyl) ethane under the conditions that the concentration of said sulfuric acid in the reaction system is not lower than 75% by weight based on the sum of the weights of said sulfuric acid and any water formed in the reaction system, the concentration of said acetaldehyde in the reaction system is maintained at 1% by weight or lower, and said isobutylbenzene is added in excess relative to said acetaldehyde;
   (II) catalytically cracking said 1,1-bis(p-isobutylphenyl) ethane in a liquid phase at reaction temperatures in the range of 200° to 350° C. in the presence of a protonic acid catalyst or in a gaseous phase at reaction temperatures in the range of 300° to 650° C. in the presence of a solid acid catalyst or a protonic acid carrying-solid acid catalyst to produce p-isobutylstyrene and isobutylbenzene as main products; and
   (III) reacting said p-isobutylstyrene with carbon monoxide and water or alcohol at temperatures in the range of 40° to 150° C. at a carbon monoxide pressure in the range of 30 to 400 kg/cm$^2$ in the presence of a metal complex carbonylation catalyst to produce α-(p-isobutylphenyl)-propionic acid or its alkyl ester.

2. The method according to claim 1, wherein at least a portion of said isobutylbenzene obtained in said step (II) is recycled to the reaction of said step (I).

3. The method according to claim 1, wherein said protonic acid in said step (II) is at least one member selected from the group consisting of inorganic acids and organic sulfonic acids.

4. The method according to claim 3, wherein said inorganic acid is at least one member selected from the group consisting of phosphoric acids, sulfuric acids and heteropoly acids.

5. The method according to claim 3, wherein said organic sulfonic acid is at least one member selected from the group consisting of naphthalenesulfonic acid and toluenesulfonic acid.

6. The method according to claim 1, wherein said solid acid in said step (II) is at least one member selected from the group consisting of clay type solid acids, synthetic silica-alumina type solid acids and zeolite type solids acids.

7. The method according to claim 1, wherein said protonic acid carrying-solid acid in said step (II) is phosphoric acid carrying-solid acid.

8. The method according to claim 1, wherein said metal of said metal complex carbonylation catalyst in said step (III) is at least one member selected from the group consisting of precious metals of Pd, Rh, Ir and Ru and Ni, Co and Fe.

9. The method according to claim 8, wherein said metal complex comprises a complex selected from the group consisting of bistriphenylphosphine dichlorocomplex, bistributylphosphine dichlorocomplex, bistricyclohexylphosphine dichlorocomplex, π-allyltriphenylphosphine dichlorocomplex, triphenylphosphine piperidine dichlorocomplex, bisbenzonitrile dichlorocomplex, biscyclohexyloxime dichlorocomplex, 1,5,9-cyclododecatriene dichlorocomplex, bistriphenylphosphine dicarbonyl complex, bistriphenylphosphine diacetate complex, bistriphenylphosphine dinitrate complex, bistriphenylphosphine sulfate complex, tetrakistriphenylphosphine complex, and complexes in which a part of the ligands therein comprise carbon monoxide.

10. The method according to claim 9 wherein said complexes in which a part of the ligands therein comprise carbon monoxide are selected from the group consisting of chlorocarbonyl bistriphenylphosphine complex, hydridocarbonyl tristriphenylphosphine complex, bischlorotetracrabonyl complex and dicarbonyl acetylacetonate complex.

11. The method according to claim 1, wherein the alcohol in said step (II) is selected from the group consisting of C$_1$–C$_4$ aliphatic alcohols.

12. The method according to claim 1, wherein the quantity of a metal complex or a compound which produces a metal complex to be used in said step (II) as a catalyst is 0.0001 to 0.5 mole per mole of said p-isobutylstyrene.

13. The method according to claim 12, wherein said quantity is 0.001 to 0.1 mole per mole of said p-isobutylbenzene.

14. The method according to claim 1, wherein the quantity of alcohol or water used in said step (II) is 0.5 to 50 parts by weight per part by weight of said p-isobutylbenzene.

15. The method according to claim 14, wherein said quantity is 1 to 20 parts by weight per part by weight of said p-oisobutylbenzene.

16. The method according to claim 1, wherein said 1,1-bis (p-isobutylphenyl) ethane is cracked in a gaseous phase in the presence of a quantity of steam which is two times or more the weight of said 1,1-bis(p-isobutylphenyl) ethane.

17. The method according to claim 1, wherein after said step (II) in which p-isobutylethylbenzene is produced as a minor product, said p-isobutylstryene is recovered by distillation and is used in said step (III).

18. The method according to claim 1, wherein said ester is further subjected to hydrolysis to produce α-(p-isobutylphenyl) propionic acid.

19. A method for producing α-(p-isobutylphenyl)-propionaldehyde which comprises the following steps of:
   (I) reacting isobutylbenzene and acetaldehyde in the presence of sulfuric acid to produce 1,1-bis (p-isobutylphenyl) ethane under the condition that the concentration of said sulfuric acid in the reaction system is not lower than 75% by weight based on the sum of the weights of sulfuric acid and any water formed in the reaction system, the concentration of said acetaldehyde in the reaction system is maintained at 1% by weight or lower, and said isobutylbenzene is added in excess relative to said acetaldehyde;
   (II) catalytically cracking said 1,1-bis(p-isobutylphenyl) ethane in a liquid phase at reaction temperatures in the range of 200° to 350° C. in the presence of a protonic acid catalyst or in a gaseous phase at reaction temperatures in the range of 300° to 650° C. in the presence of a solid acid catalyst or a protonic acid carrying-solid acid catalyst to produce p-isobutylstyrene and isobutylbenzene as main products; and
   (III) reacting said p-isobutylstyrene with carbon monoxide and hydrogen at temperatures in the range of 40° to 150° C. at a reaction pressure in the range of 5 to 500 kg/cm$^2$ in the presence of a metal complex carbonylation catalyst to produce α-(p-isobutylphenyl)-propionaldehyde.

20. A method for producing α-(p-isobutylphenyl)propionic acid which comprises the following steps of:
   (I) reacting isobutylbenzene and acetaldehyde in the presence of sulfuric acid to produce 1,1-bis(p-isobutylphenyl) ethane under the conditions that the concentration of said sulfuric acid in the reaction system is not lower than 75% by weight based on the sum of the weights of said sulfuric acid and any water in the reaction system, the concentration of said acetaldehyde in the reaction system is maintained at 1% by weight or lower, and said isobutylbenzene is added in excess relative to said acetaldehyde.
   (II) catalytically cracking said 1,1-bis(p-isobutylphenyl) ethane in a liquid phase at reaction temperatures in the range of 200° to 350° C. in the presence of a protonic acid catalyst or in a gaseous phase at reaction temperatures in the range of 300° to 650° C. in the presence of a solid acid catalyst or a protonic acid carrying-solid acid catalyst to produce p-isobutylsytrene and isobutylbenzene as main products;
   (III) reacting said p-isobutylstyrene with carbon monoxide and hydrogen at temperatures in the range of 40° to 150° C. at a reaction pressure in the range of 5 to 500 kg/cm$^2$ in the presence of a metal complex carbonylation catalyst to produce α-(p-isobutypheneyl)-propionaldehyde; and
   (IV) oxidizing said α-(p-isobutylphenyl)propionaldehyde to produce α-(p-isobutylphenyl) propionic acid.

21. The method according to claim 20, wherein at least a part of said isobutylbenzene obtained in said step (II) is recycled to the reaction of said step (I).

22. The method according to claim 20, wherein said protonic acid in said step (II) is at least one member selected from the group consisting of inorganic acids and organic sulfonic acids.

23. The method according to claim 22, wherein said inorganic acid is at least one member selected from the group consisting of phosphoric acids, sulfuric acids and heteropoly acids.

24. The method according to claim 22, wherein said organic sulfonic acid is at least one member selected from the group consisting of naphthalenesulfonic acid and toluenesulfonic acid.

25. The method according to claim 20, wherein said solid acid in said step (II) is at least one member selected from the group consisting of clay type solid acids, synthetic silica-alumina type solid acids and zeolite type solid acids.

26. The method according to claim 20, wherein said protonic acid carrying-solid acid in said step (II) is phosphoric acid carrying-solid acid.

27. The method according to claim 20, wherein said metal of said metal complex carbonylation catalyst in said step (III) is at least one member selected from the group consisting of precious metals of Pd, Rh, Ir and Ru and Ni, Co and Fe.

28. The method according to claim 27, wherein said metal complex comprises a complex selected from the group consisting of bistriphenylphosphine dichlorocomplex, bistributylphosphine dichlorocomplex, bistricyclohexylphosphine dichlorocomplex, π-allyltriphenylphosphine dichlorocomplex, triphenylphosphine piperidine dichlorocomplex, bisbenzonitrile dichlorocomplex, biscyclohexyloxime dichlorocomplex, 1,5,9-cyclododecatriene dichlorocomplex, bistriphenylphosphine dicarbonyl complex, bistriphenylphosphine diacetate complex, bistriphenylphosphine dinitrate complex, bistriphenylphosphine sulfate complex, tetrakistriphenylphosphine complex, and complexes in which a part of the ligands therein comprise carbon monoxide.

29. The method according to claim 28 wherein said complexes in which a part of the ligands therein comprise carbon monoxide are selected from the group consisting of chlorocarbonyl bistriphenylphosphine complex, hydridocarbonyl tristriphenylphosphine complex, bischlorotetracarbonyl complex and dicarbonyl acetylacetonate complex.

30. The method according to claim 20, wherein said oxidization of said step (IV) is carried out by a mild oxidizing agent.

31. The method according to claim 30, wherein said oxidizing agent is a hypohalogenous acid salt.

32. The method according to claim 20, wherein said 1,1-bis(p-isobutylphenyl)ethane is cracked in a gaseous phase in the presence of a quantity of steam which is two times or more the weight of said 1,1-bis(p-isobutylphenyl)ethane.

33. The method according to claim 20, wherein, after said step (II) in which p-isobutylethylbenzene is produced as a minor product, said p-isobutylstyrene is recovered by distillation and is used in said step (III).

* * * * *